United States Patent
Morrissey et al.

(10) Patent No.: US 9,138,564 B2
(45) Date of Patent: Sep. 22, 2015

(54) CATHETER ASSEMBLY

(71) Applicant: Applied Medical Technology Ltd., Cambridge (GB)

(72) Inventors: Ray Morrissey, Cambridge (GB); Serge Barneaud, Cambridge (GB)

(73) Assignee: Applied Medical Technology Ltd., Cambridge (GB)

( * ) Notice: Subject to any disclaimer, the term of this patent is extended or adjusted under 35 U.S.C. 154(b) by 0 days.

(21) Appl. No.: 14/257,324

(22) Filed: Apr. 21, 2014

(65) Prior Publication Data

US 2014/0336583 A1 Nov. 13, 2014

(30) Foreign Application Priority Data

Apr. 22, 2013 (GB) .................................. 1307203.8

(51) Int. Cl.
*A61M 25/06* (2006.01)
*A61M 25/02* (2006.01)

(52) U.S. Cl.
CPC ....... *A61M 25/0631* (2013.01); *A61M 25/0606* (2013.01); *A61M 25/02* (2013.01)

(58) Field of Classification Search
CPC ............ A61M 5/178; A61M 25/0631; A61M 25/0606; A61M 25/02; A61B 17/3415
USPC ............. 604/164.01, 164.04, 164.08, 164.12, 604/174, 192, 198, 263
See application file for complete search history.

(56) References Cited

U.S. PATENT DOCUMENTS

| 5,522,803 | A | 6/1996 | Teissen-Simony |
| 2002/0165497 | A1 | 11/2002 | Greene |
| 2004/0158207 | A1* | 8/2004 | Hunn et al. .............. 604/164.01 |

FOREIGN PATENT DOCUMENTS

WO 98/30268 A1 7/1998
WO 2009/007742 1/2009

OTHER PUBLICATIONS

Search Report from British Patent Application No. GB1307203.8, dated on Oct. 8, 2013.
Extended European Search Report from EP Patent Application No. 14164798.2 dated Aug. 8, 2014.

* cited by examiner

*Primary Examiner* — Theodore Stigell
*Assistant Examiner* — Amber Stiles
(74) *Attorney, Agent, or Firm* — Stroock & Stroock & Lavan LLP (57) ABSTRACT

A catheter assembly is disclosed herein including a hub assembly and a needle retracting device. The hub assembly includes a hub and a catheter attached to the hub. The needle retracting device releasably attached to the hub assembly and arranged to project a needle through the catheter for catheterization and to retract the needle and allow detachment from the hub assembly. The needle retracting device includes a chassis extending from a base and a slider carrying the needle supported on the chassis. The slider arranged to move away from the base from a position in which the needle projects through the catheter to a position in which the needle is withdrawn from the catheter and shielded by the chassis. The chassis and hub include movable locking members and cooperating locking surfaces for engaging the locking members. The slider includes retaining surfaces for limiting movement of the locking members.

13 Claims, 12 Drawing Sheets

CATHETER ASSEMBLY

CROSS-REFERENCE TO RELATED APPLICATIONS

This application claims the benefit of priority from United Kingdom Patent Application No. 1307203.8, filed on Apr. 22, 2013, the entire contents of which are incorporated herein by reference.

FIELD OF THE INVENTION

The present invention relates to a catheter assembly.

BACKGROUND

Treatment of some medical conditions involves administering a drug (or a combination of drugs) subcutaneously or intravenously into a patient.

A drug delivery system can be divided in two parts, namely a device for supplying the drug (such as a bag, pump or syringe) and a tubing arrangement for delivering the drug into the patient.

The tubing arrangement includes a soft cannula or catheter. One end of the catheter is inserted into the patient, leaving the other end available for connection to the drug-supplying device. The catheter is held in place by taping the cannula to the surface of the skin of the patient or by using a housing which itself is attached to the surface of the skin.

To insert the catheter into the patient, a device is used which employs an introducer needle, for example as described in U.S. Pat. No. 5,522,803 A. The catheter is carried on the needle such that, when the needle pierces the skin and underlying tissue, the catheter is also inserted. The needle is then withdrawn, leaving the catheter in place.

Most existing insertion devices suffer the drawback that the needle is often exposed before and/or after insertion, thereby allowing possible contamination of the needle and exposing the operator to so-called "needle stick" injury, which carries with it a risk of infection.

One solution is to use protective elements to shield the needle.

For example, US 2004/0158207 A1 describes a device for inserting a cannula which is connected to a base body. The device includes a frame which is used to accommodate the cannula and an operating element which is used to move the cannula out of the protective element.

Although the device can reduce the chance of needle stick injury, the device can be detached from the base body with the needle is still exposed.

WO 2009/007742 A1 describes a cannula insertion device comprising an insertion device in which the needle is shielded before and after it is inserted. The insertion device can only be detached after the needle has been drawn back into the body of the insertion device.

SUMMARY

The present invention seeks to provide a simple device which can still help to protect a user from possible needle stick injury after insertion of a catheter.

According to a first aspect of the present invention is there provided a catheter assembly comprising a hub assembly comprising a hub and a catheter attached to the hub and a needle retracting device releasably attached to hub assembly which is arranged to project a needle through the catheter to allow catheterization and, in response to user actuation, to retract the needle and to be detached or to allow detachment from the hub assembly.

The needle retracting device comprises a chassis extending along an axis from a base and a slider which carries the needle supported on the chassis. The slider is arranged to be moveable away from the base along the axis from a first position in which the needle projects through the catheter to a second position in which the needle is withdrawn from the catheter and is shielded by the chassis. The chassis and hub comprise movable locking members and cooperating locking surfaces for engaging the locking members. The slider comprises retaining surfaces for limiting movement of the locking members. The catheter assembly is configured such that when the slider is in the first position, the locking members are discouraged or prevented from disengaging from the locking surfaces by the retaining surfaces and when the slider is in the second position, the locking members are free to disengage from the locking surfaces and so allow the needle retracting device to disengage from the hub assembly.

Thus, once the catheter has been inserted, user actuation to retract the needle causes the retaining surfaces to be removed and so allow the needle retracting device to be released from the hub assembly.

The catheter assembly may comprise the chassis, the slider, and an actuator which is configured to move the slider. The catheter assembly may further comprise a spring.

The chassis may comprise the locking members and the hub may comprise the locking surface. Locking members and/or locking surfaces may be referred to as "latching projections". The locking members may each comprise a catch comprising a hinged arm and a barbed head. The hinged arm may be biased away from retention/towards release. Thus, when the retaining surfaces are not present, the head springs away from the locking surface.

The locking surfaces may each comprise a recess and/or a projection providing a lip. For example, two (or more) separate recesses may be provided on opposite sides of (or around) the hub. The locking surfaces may comprise a single groove running below a rim of the hub forming a continuous lip.

The chassis may comprise a tubular body extending from the base portion to a distal end along the axis.

The slider may comprise a tubular (or annular body) disposed outside the tubular body of the chassis, a hub carrying the needle disposed inside the tubular body of the slider (but projecting out of the body) and member(s) connecting the hub to the annular body. An inner wall of the tubular body of the slider may provide the retaining surfaces.

The tubular body may comprise slots (or "cut-outs") for receiving and guiding the connecting members. Each slot may comprise a start, a first section and a second section. The first section may extend from the start and the second follows the first section. The second section may extend away from the base portion towards the distal end and may be orientated so as to allow the slider to move along the tubular body.

The first section may be orientated so as to allow the slider to rotate within the tubular body without moving along the tubular body. Thus, this can be used to provide initial tactile feedback.

The catheter assembly may further comprise a cap-like actuator disposed over the distal end of the tubular body and a distal end of the slider. The actuator may be configured to rotate from a first angular position and rotational movement may be communicable to the slider.

The slider and actuator may be configured such that rotational movement of the actuator from a first angular position to a second angular position is not communicated to the slider.

This can be used to provide tactile feedback, i.e. that the user is properly turning the actuator and help to prevent inadvertent retraction of the needle.

The slider and actuator may be configured such that rotational movement of the actuator from the second angular position to a third angular position is communicated to the slider and causes rotation of the slider without substantial movement along the tubular body. Thus, the needle rotates and this can help to overcome stiction.

The slider and actuator may be configured such that further rotational movement from the third angular position causes the slider to move along the tubular body.

The actuator may include a window and the slider may include an indicator. The actuator and slider may be configured such that the indicator appears in the window when the slider is in the second position.

The catheter assembly may further comprise a spring biasing the slider away from the base.

The hub assembly may include a port in fluid communication with the catheter.

According to a second aspect of the present invention there is provided a catheter assembly comprising a hub assembly comprising a hub and a catheter attached to the hub and a needle retracting device releasably attached to hub assembly which is arranged to project a needle through the catheter to allow catheterization and, in response to user actuation, to retract the needle and to be detached or to allow detachment from the hub assembly.

The needle retracting device may comprise a chassis extending along an axis from a base and a slider which carries the needle supported on the chassis. The slider is arranged to be moveable away from the base along the axis from a first position in which the needle projects through the catheter to a second position in which the needle is withdrawn from the catheter and is shielded by the chassis. The needle retracting device may further comprise a cap-like actuator. The actuator may be configured to cause the slider to move along the axis.

The actuator may be configured to rotate from a first angular position and rotational movement may be communicable to the slider.

The slider and actuator may be configured such that rotational movement of the actuator from a first angular position to a second angular position is not communicated to the slider. This can be used to provide tactile feedback, i.e. that the user is properly turning the actuator and help to prevent inadvertent retraction of the needle.

The slider and actuator may be configured such that rotational movement of the actuator from the second angular position to a third angular position is communicated to the slider and causes rotation of the slider without substantial movement along the tubular body. Thus, the needle rotates and this can help to overcome stiction.

The slider and actuator may be configured such that further rotational movement from the third angular position causes the slider to move along the tubular body.

According to a third aspect of the present invention there is provided a method of operating the catheter assembly. The method comprises inserting the catheter and needle, retracting the needle and detaching the needle retracting device from the hub assembly.

The catheter assembly may comprise an actuator cap and the method may comprise rotating the actuator cap so as to retract the needle.

BRIEF DESCRIPTION OF THE DRAWINGS

Certain embodiments of the present invention will now be described, by way of example, with reference to the accompanying drawings, in which:

FIGS. 22a to 22f are front perspective views of the catheter assembly shown in FIG. 1 during operation;

FIGS. 23a to 23f are sectional views of the catheter assembly shown in FIG. 1 during operation.

DETAILED DESCRIPTION OF CERTAIN EMBODIMENTS

Catheter Assembly 1

Referring to FIGS. 1 to 5, a catheter assembly 1 forming part of an infusion set is shown in an as-supplied, ready-to-use state. The catheter assembly 1 is intended for single use and is used to insert a soft catheter 2 subcutaneously using a needle 3 (also referred to as an "introducer" or "inserter").

Figure 22:
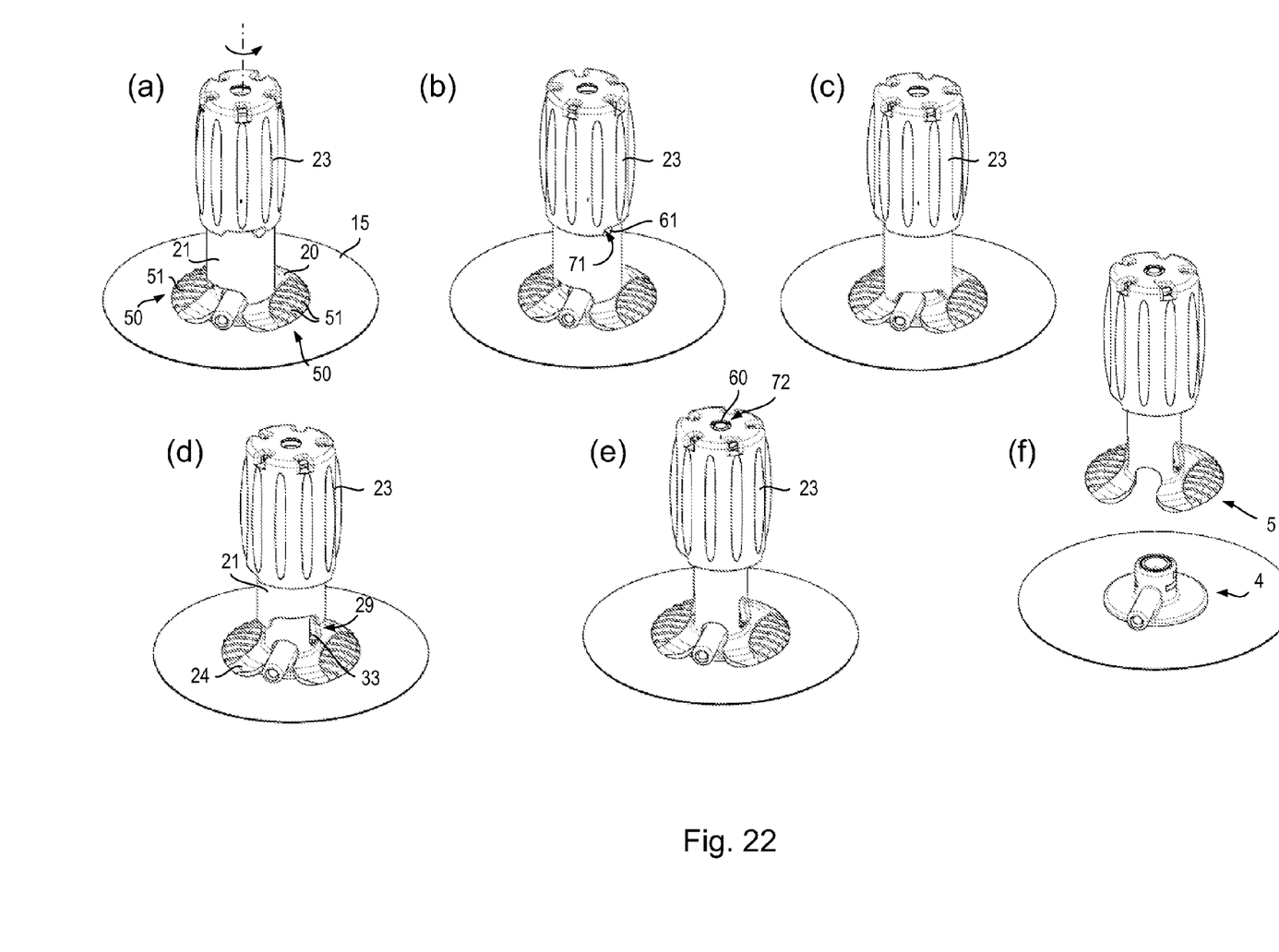

The catheter assembly 1 generally comprises two main parts, namely a hub assembly 4 and a needle retracting device 5 (best shown in FIG. 22f).

Hub Assembly 4

Figure 1:
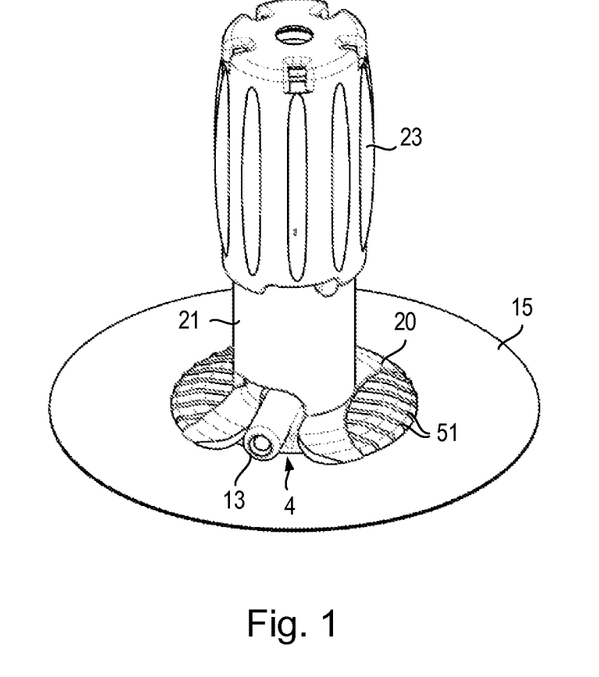
FIG. 1 is a perspective view of a catheter assembly.
Figure 2:
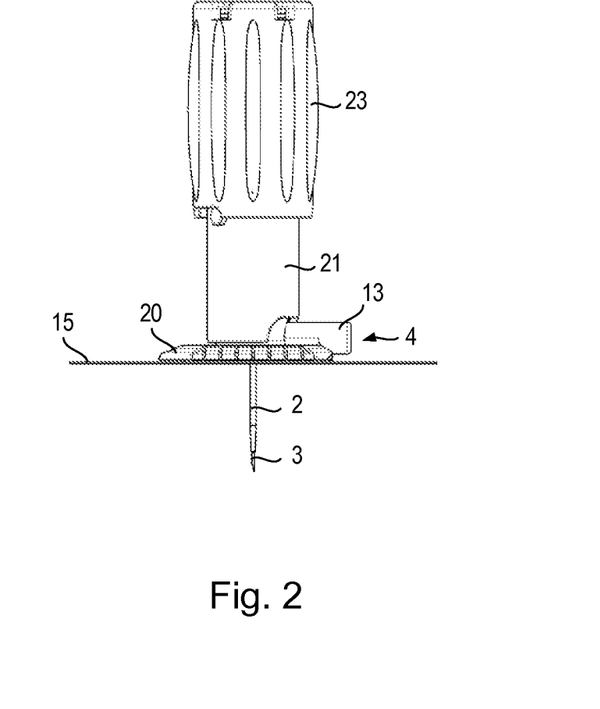
FIG. 2 is a side view of the catheter assembly shown in FIG. 1.
Figure 3:
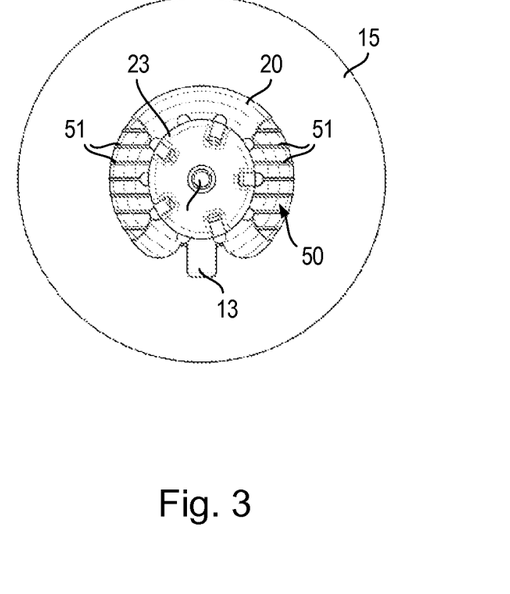
FIG. 3 is a plan view of the catheter assembly shown in FIG. 1.
Figure 4:
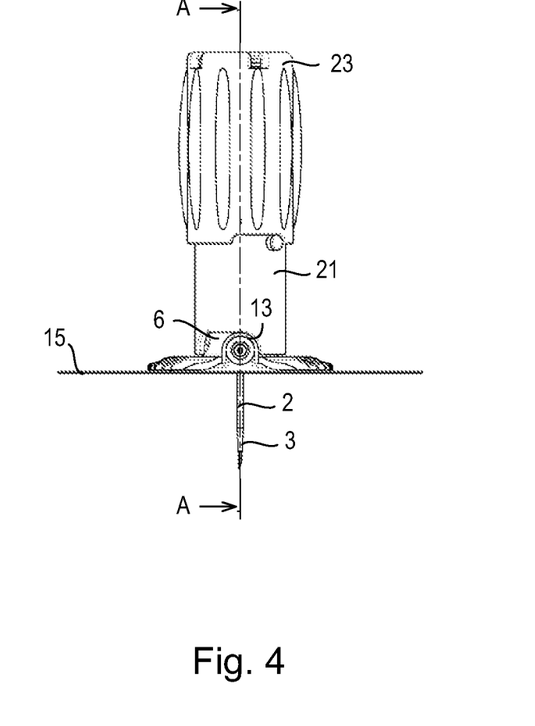
FIG. 4 is an end view of the catheter assembly shown in FIG. 1.
Figure 5:
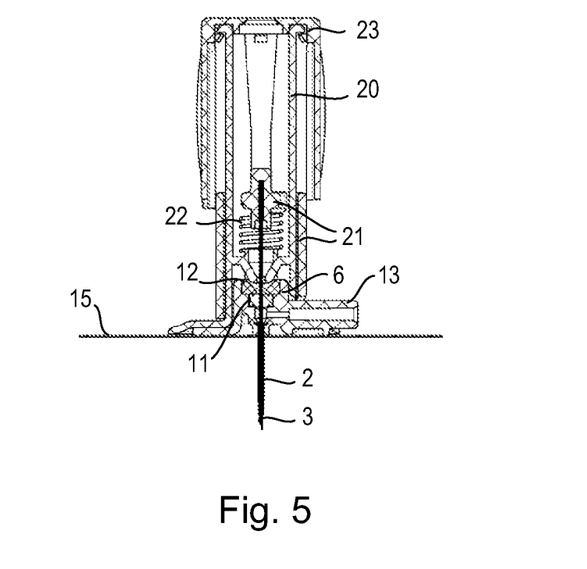
FIG. 5 is a cross sectional view of the catheter assembly shown in FIG. 4 taken along the line A-A.
Figure 6:
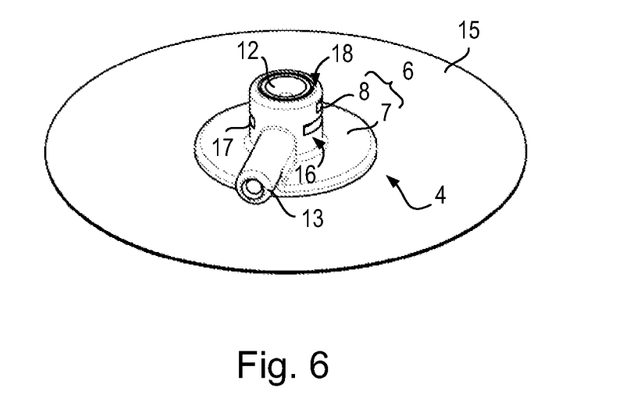
FIG. 6 is a perspective view of a hub assembly.
Figure 7:
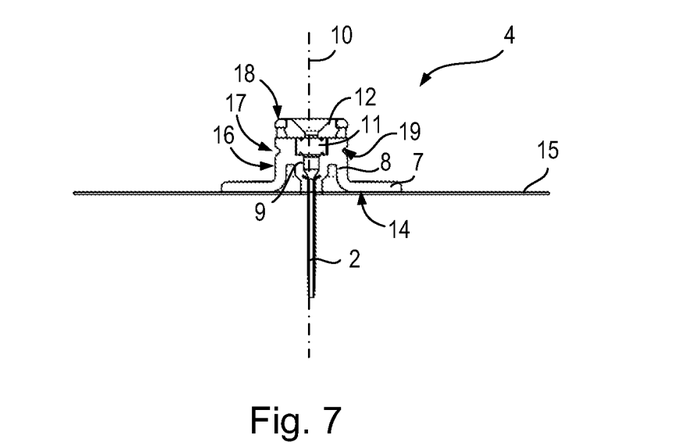
FIG. 7 is a cross sectional view of the hub assembly shown in FIG. 6.

Referring also to FIGS. 6 and 7, the hub assembly 4 comprises a nipple-shaped hub 6 which includes a flat, circular base 7 supporting a short, tubular projection 8 (herein also referred to as the "septum housing" or "hub connector") upstanding from the base 7 having a stepped bore 9 along a central axis 10.

A septum 11 is housed in an upper part of the bore 9 and is held in place by an annular cap 12 having an inwardly tapping inner wall. The septum housing 8 has a side port 13 in fluid communication with a lower part of the bore 9. A tube (not shown) may be attached to the port 13.

The catheter 2 depends from an underside 14 of the hub assembly 4 and is orientated along the central axis 10. Thus, the catheter 2 extends generally perpendicularly from the underside 14 of the hub assembly 4. The hub assembly 4 is attached to an upper surface of an adhesive pad 15 which can be used to affix the hub assembly 4 to the surface of the skin of a patient (not shown).

The septum housing 8 has a cylindrical outer sidewall 16 which includes a pair of arcuate (i.e. around the circumference) grooves 17 on opposite sides of the septum housing 8 between the base 7 and the top 18 of the septum housing 8. As will be explained in more detail later, the grooves 17 provides locking surfaces 19 which secures the needle retracting device 5 to the hub assembly 4.

The catheter 2 is made from a flexible plastic material, such as polytetrafluoroethylene (PTFE). The hub 5 is made from a thermoplastic, such as polybutylene terephthalate (PBT) or polypropylene (PP). The septum 11 is made from a resilient, self-sealing material, such as silicone. The annular septum cap 12 is made from a thermoplastic, such as acrylonitrile butadiene styrene (ABS).

The needle retracting device 5 is releasably attached to the hub assembly 4. In the as-supplied, ready-to-use state, the needle retracting device 5 projects the needle 3 through the catheter 2 such that the distal end of the needle projects from the catheter 2 thereby allowing catheterization.

As will be explained in more detail later, after the catheter 2 has been inserted, a user (which is typically a carer, but could be the patient) operates the needle retracting device 5 to retract the needle 3 and separate the needle retracting device 5 from the hub assembly 4.

Needle Retracting Device 5

The needle retracting device 5 comprises a chassis 20 (or "frame"), a slider 21 which is supported on the chassis 20 and which carries the needle 3, a spring 22 (for example, formed from stainless steel) and an actuator cap 23.

Chassis 20

Referring to FIGS. 1 to 5 and also to FIGS. 8 to 11, the chassis 20 comprises a shallow-domed base 24 and an upstanding tubular body 25. The tubular body 25 extends along a central axis 26 from the base 24.

Figure 8:
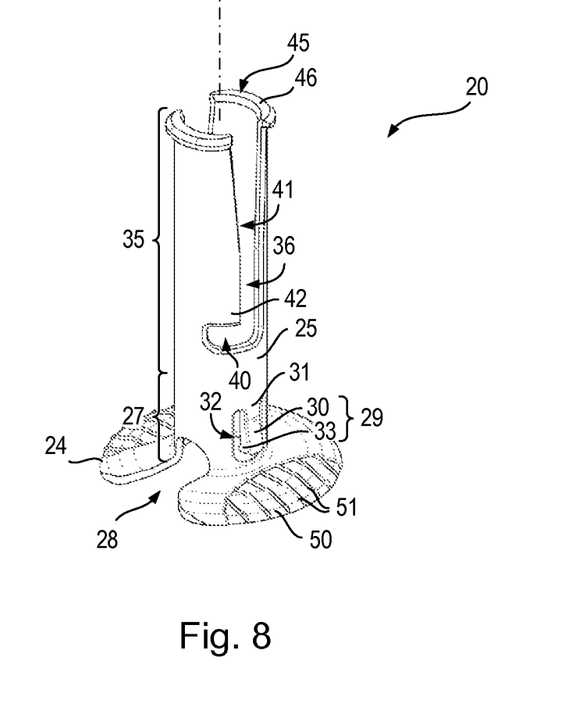
FIG. 8 is a perspective view of a chassis.
Figure 9:
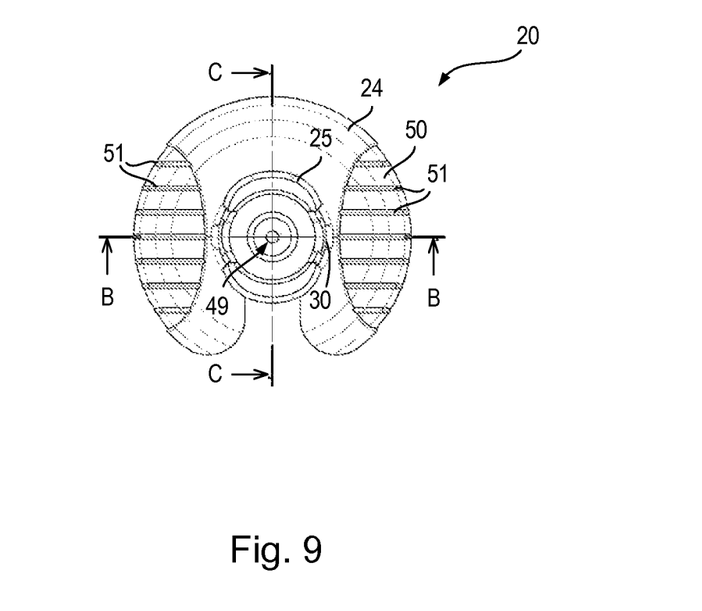
FIG. 9 is a plan view of the of the chassis shown in FIG. 8.

The chassis 20 sits on top of the hub assembly 4 (FIG. 6). The dome-shaped base 24 provides a space to accommodate the base 7 (FIG. 6) of the hub assembly 4 (FIG. 6). A lower portion 27 of the chassis 20 accommodates the septum housing 8 (FIG. 6). The base 24 of the chassis 20 and a part of the lower portion 27 of the tubular body 25 includes a cut-out 28 to accommodate the side port 13 (FIG. 6).

The lower portion 27 of the tubular body 25 includes a pair of catches 29 on opposite sides of the chassis 20. The catches 29 are arranged to cooperate with corresponding grooves 17 (FIG. 6) on the hub assembly 4 (FIG. 6). Each catch 29 comprises a resilient arm 30 depending from a flexible point of attachment 31 with the chassis 20 formed by a 'U'-shaped slot 32 in the tubular body 25. Each catch 29 includes an inwardly-directed barbed head 33. Each arm 30 is outwardly angled so that the barbed head 33 does not protrude or excessively protrude beyond an inner perimeter 34 of the tubular body 25. The barbed heads 33 can be pushed towards each other by applying an inwardly-directed force on each arm 30 thereby causing engagement of the barbed heads 33 and the grooves 17 (FIG. 6) and so latch the chassis 20 (and, thus, the needle retracting device 5) and the hub assembly 4. The grooves 17 (particularly the ends of the grooves 17) and barbed heads 33 also discourage or prevent rotation of the chassis 20 with respect to the hub assembly 4 during needle retraction.

An upper portion 35 of the tubular body 25 includes a pair of 'L'-shaped slots 36. Each slot 36 includes a start 37, a bend 38 and an (open) end 39.

A first slot section 40 extends circumferentially through a 45° arc from the start 37 to the bend 38. The circumferential slot sections 40 have the same sense, i.e. they extend from the start 37 to the bend 38 in the same direction, which in this case is anti-clockwise.

A second slot section 41 extends lengthwise (i.e. along the tubular body 25) from the bend 38 to the end 39 which is at the top of the tubular body 25.

For each slot 36, a corner 42 is formed at the bend 38. As will be explained in more detail later, movement of the slider 21 away from the base 24 and along the tubular body 25 can occur once cross members 58 (FIG. 12) forming part of the slider 21 clear the corners 42.

The second slot section 41 tapers slightly outwardly from approximately midway along the section 41 to the end 39.

The slots 36 form a pair of upwardly-projecting curved fins 44. The tops 45 of the fins 44 have outwardly-projecting lips 46 which are used to snap-fit the chassis 20 to the actuator cap 23.

Figure 10:
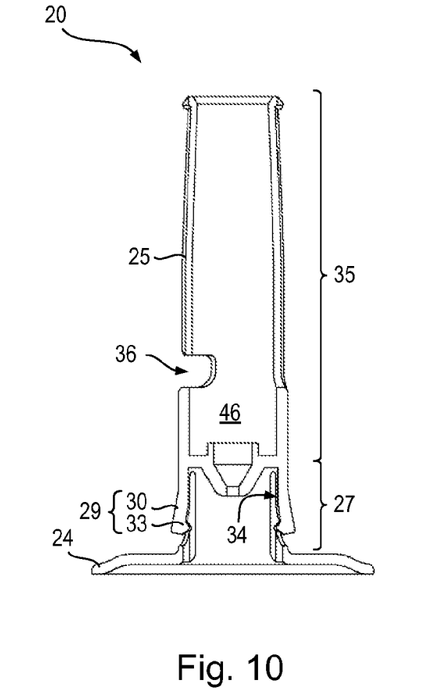
FIG. 10 is a cross sectional view of the chassis shown in FIG. 9 taken along the line B-B.
Figure 11:
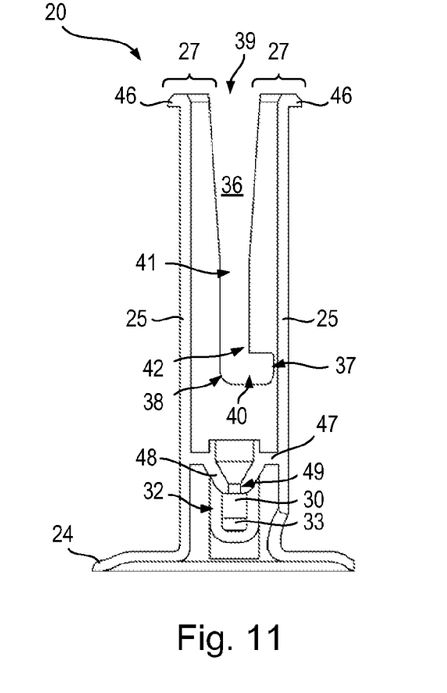
FIG. 11 is a cross sectional view of the chassis shown in FIG. 9 taken along the line C-C.

The tubular body 25 provides a lumen 46 which is divided into two parts by a dividing floor 47 and dome 48 having a funnel-shaped inner wall and an aperture 49 for accommodating the needle 3. The floor 47 and dome 48 provide a guard which helps to limit access to the needle 3 when retracted.

Two elliptical regions 50 on the upper surface of the base 24 on either side of the tubular body 25 have a set of ribs 51. The ribs 51 can help the user to hold the catheter assembly 1 in place while twisting the actuator cap 23.

The chassis 20 is made from a thermoplastic, such as polyoxymethylene (POM). The chassis 20 is formed as a single piece, for example, by injection moulding.

Slider 21

Referring to FIGS. 1 to 5 and also to FIGS. 12 to 15, the slider 21 comprises a tubular body 52 having a central axis, a first, lower end 53 and a second, upper end 54.

Figure 12:
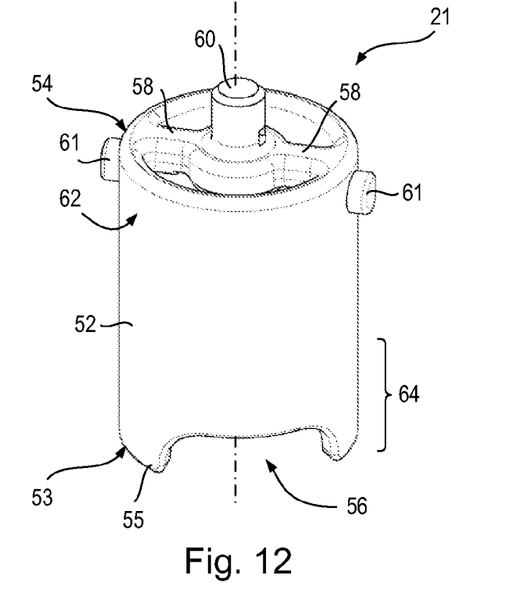
FIG. 12 is a perspective view of a slider.
Figure 13:
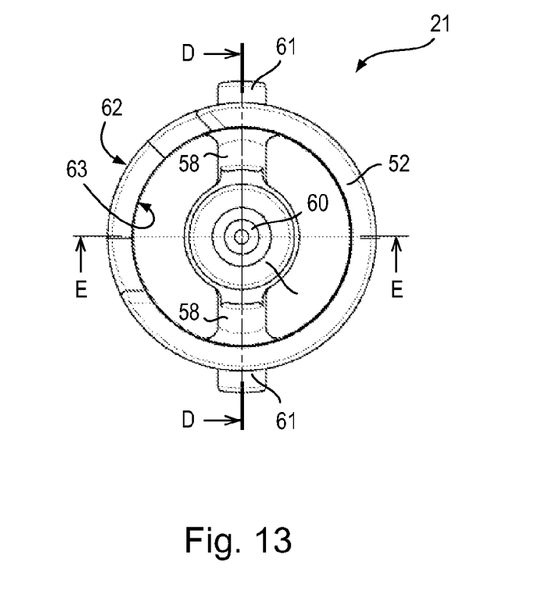
FIG. 13 is a plan view of the slider shown in FIG. 12.

The first end 53 of the tubular body 52 is open. The first end 53 has generally circular edge 55 having a shallow cut-out or raised edge 56. The raised edge 56 extends circumferentially approximately through a 45° arc. The raised edge 56 serves to accommodate the side port 13 and is elongated so as to allow the slider 21 to rotate with respect to the hub assembly 4 (FIG. 6).

The second end 54 of the tubular body 52 is open. A hub or block 57 is disposed in the centre of the open end 54 and is connected to the tubular body 52 by first and second cross members 58.

The hub 57 includes a bore 59 for receiving the needle 3. The needle 3 is secured in the bore 59 by moulding or gluing.

Figure 16:
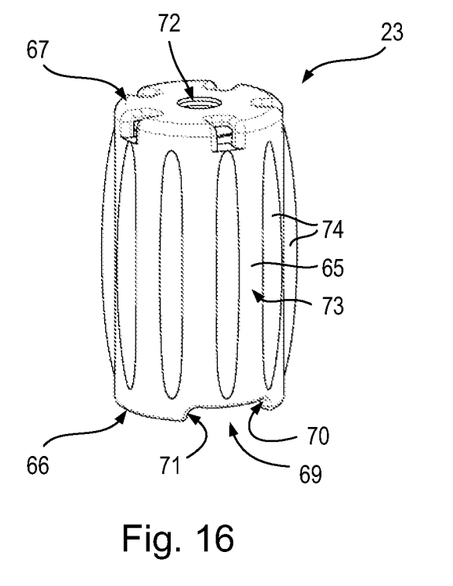
FIG. 16 is a front, upper perspective view of an actuator cap.
Figure 17:
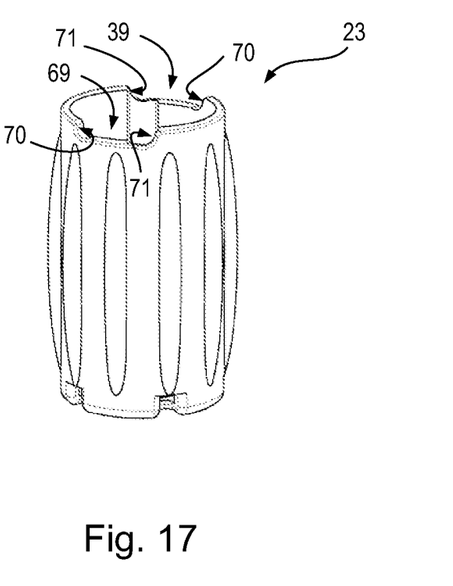
FIG. 17 is a front, lower perspective view of the actuator cap shown in FIG. 16.

An axial projection 60 from the hub 57 serves as indicator. As will be explained later, when the slider 21 is retracted, the indicator 57 projects into a window 72 (best shown in FIG. 16) in the actuator cap 23 thereby signalling to the user that needle 3 has been fully retracted.

The slider 21 includes first and second force-receiving members 61. In this example, the force-receiving members 61 are off the central axis and take the form of bosses or short pins. The members 61 project radially outwardly from an outer sidewall 62 of the tubular body 52 at (or close to) the second end 54 of the tubular body 52. As will be explained in more detail later, the force-receiving members 61 engage with the actuator cap 23 as it rotates and cause the slider 21 to rotate with the actuator cap 23.

Figure 14:
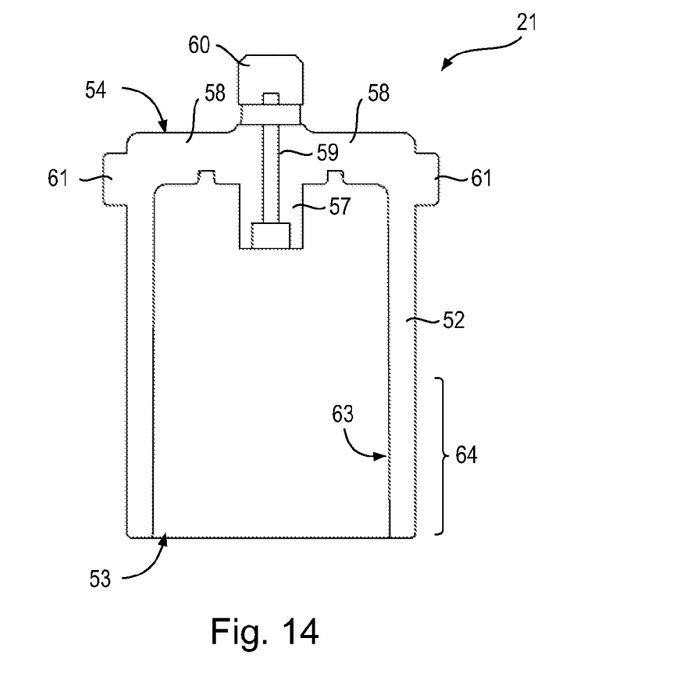
FIG. 14 is a cross sectional view of the slider shown in FIG. 13 taken along the line D-D.
Figure 15:
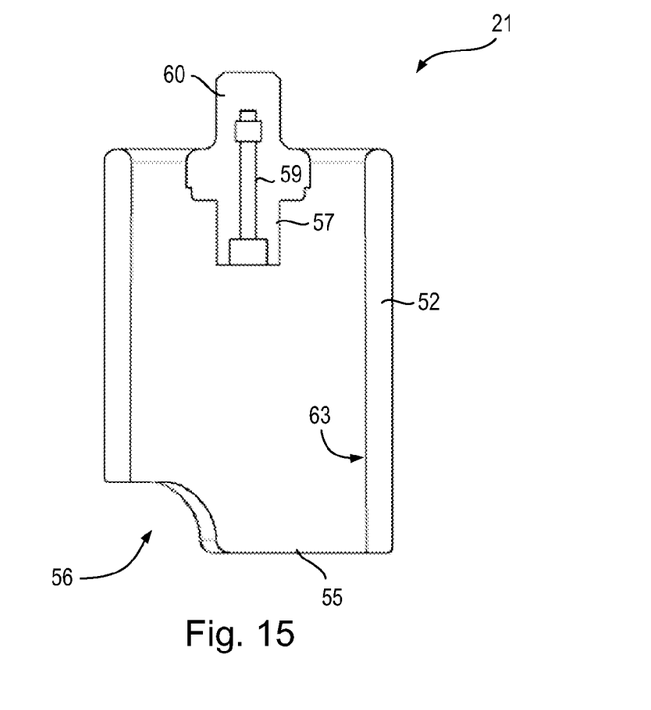
FIG. 15 is a cross sectional view of the slider shown in FIG. 13 taken along the line E-E.

An inner wall 63 of the tubular body 52 in a lower part 64 of the tubular body 52 provides a retaining surface (in the form of a collar) for acting on the catches 29. As will be explained in more detail later, when slider 21 is in a first, lower position, the wall 63 urge the catches 29 inwards to engage the grooves 17. When the slider 21 moves sufficiently away from the base 24 (FIG. 8), the wall 63 clears the catches 29 and so the catches 29 disengage (or are able to disengage) the grooves 17.

The slider 21 is made from a thermoplastic, such as ABS. The slider 21 is formed as a single piece, for example, by injection moulding. The needle 3 is made from stainless steel, for example, AISI 304 grade stainless steel.

Actuator Cap 23

Referring to FIGS. 1 to 5 and also to FIGS. 16 to 21, the actuator cap 23 comprises a generally tubular body 65 having a first, lower end 66 and a second, upper end 67.

The first end 66 of the tubular body 65 is open. The first end 66 has generally circular edge 68 having first and second shallow cut-outs 69 (best shown in FIG. 17). Each cut-out 69 extends circumferentially approximately through a 45° arc. Each cut-out 69 extends from a start 70 to an end 71. Each end 71 provides a force-transmitting surface which moves to engage with and then apply force to a corresponding force-receiving member 61 on the slider 21.

The second end 67 of the tubular body 65 is generally closed but includes a window or aperture 72 into which indicator 60 (FIG. 12) can project.

Figure 20:
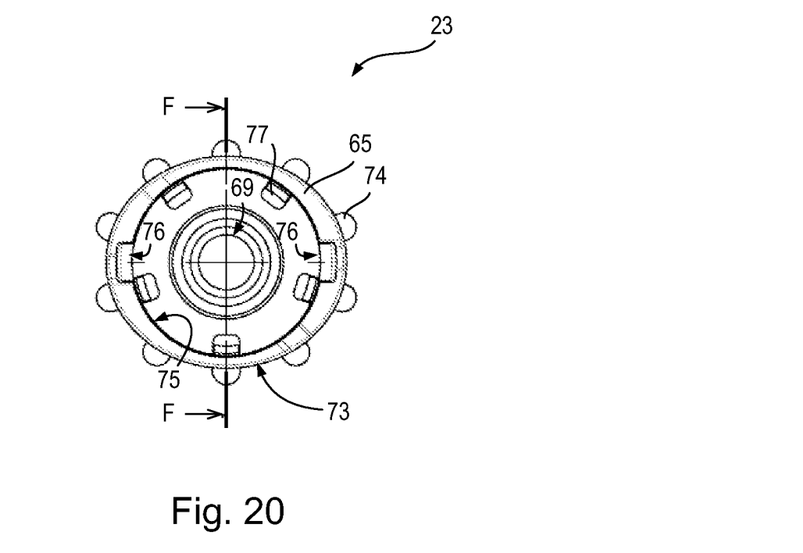
FIG. 20 is a bottom side view of the actuator cap shown in FIG. 16.
Figure 21:
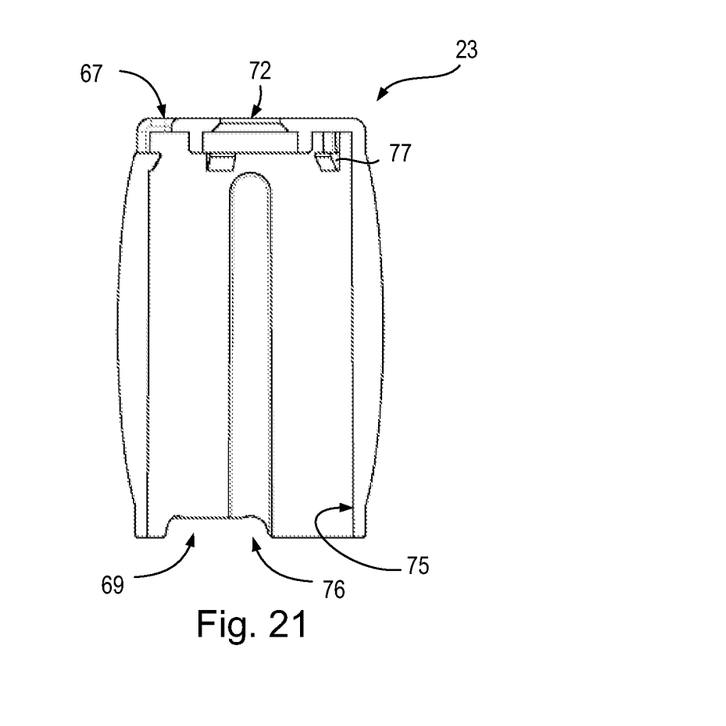
FIG. 21 is a cross sectional view of the actuator cap shown in FIG. 16 taken along the line F-F.

The tubular body 65 has an outer sidewall 73 which is generally elliptical in plan view (which is best shown in FIG. 20) and supports angularly spaced ribs 74 which run lengthwise. The elliptical profile and the ribs 74 can help the user to grip and twist the actuator cap 23.

The tubular body 65 has an inner sidewall 75 which is generally circular in plan view (best shown in FIG. 20). First and second grooves 76 run lengthwise along the inner sidewall 75 on opposite sides. The grooves 76 are aligned with the end of the raised edges 69 at the bottom of the actuator cap 23. Thus, when the force-receiving members 61 are aligned with the grooves 76 and the slider 21 has rotated sufficiently for the cross members 58 (FIG. 12) to clear the corner 42 (FIG. 11) of the slot 36, the slider 21 is urged away from chassis base 24 (FIG. 11) and the force-receiving members 61 travel along the grooves 76.

Inside the actuator cap 23 close to the second end 67, a set of angularly-spaced, inwardly-projecting barbed heads 77 are provided to non-releasably snap-fit with projecting lips 46 (FIG. 11) on the chassis 20.

The actuator cap 23 is made from a thermoplastic, such as ABS. The actuator cap 23 is formed as a single piece, for example, by injection moulding.

Assembly

Referring again to FIGS. 1 to 5, the catheter assembly 1 is assembled by attaching the chassis 20 to the hub assembly 4, dropping the spring 22 into the chassis 20, inserting the slider 21 such that the needle 3 passes into the catheter 2 such that the distal end of the needle comes out of the catheter 2, turning the slider 21 such that the cross members 58 (FIG. 12) enter the first section 40 (FIG. 8) of slot 36 (FIG. 8) and pressing the actuator cap 23 onto the chassis 20 until the lips 46 (FIG. 12) of the chassis 20 and the barbed heads 77 (FIG. 21) inside the actuator cap 23 snap fit.

The spring 22 takes the form of a coil spring and is made from stainless steel.

Operation

Referring to FIGS. 22*a* to 22*f* and FIGS. 23*a* to 23*f*, operation of the catheter assembly 1 will now be explained.

The catheter assembly 1 is removed from its packaging (not shown).

The user (not shown) removes a central strip of backing paper (not shown) from the underside of adhesive tape 15 leaving two segments of the backing paper either side of the catheter 2. A protective sleeve (not shown) is removed from the catheter.

The user offers up and inserts the catheter 2 and inserter needle 3 into the skin of the patient (not shown). The user can remove the remaining segments of backing paper so as to secure the hub assembly 4 to the skin of the patient.

The user can then retract the needle 3.

Figure 23:
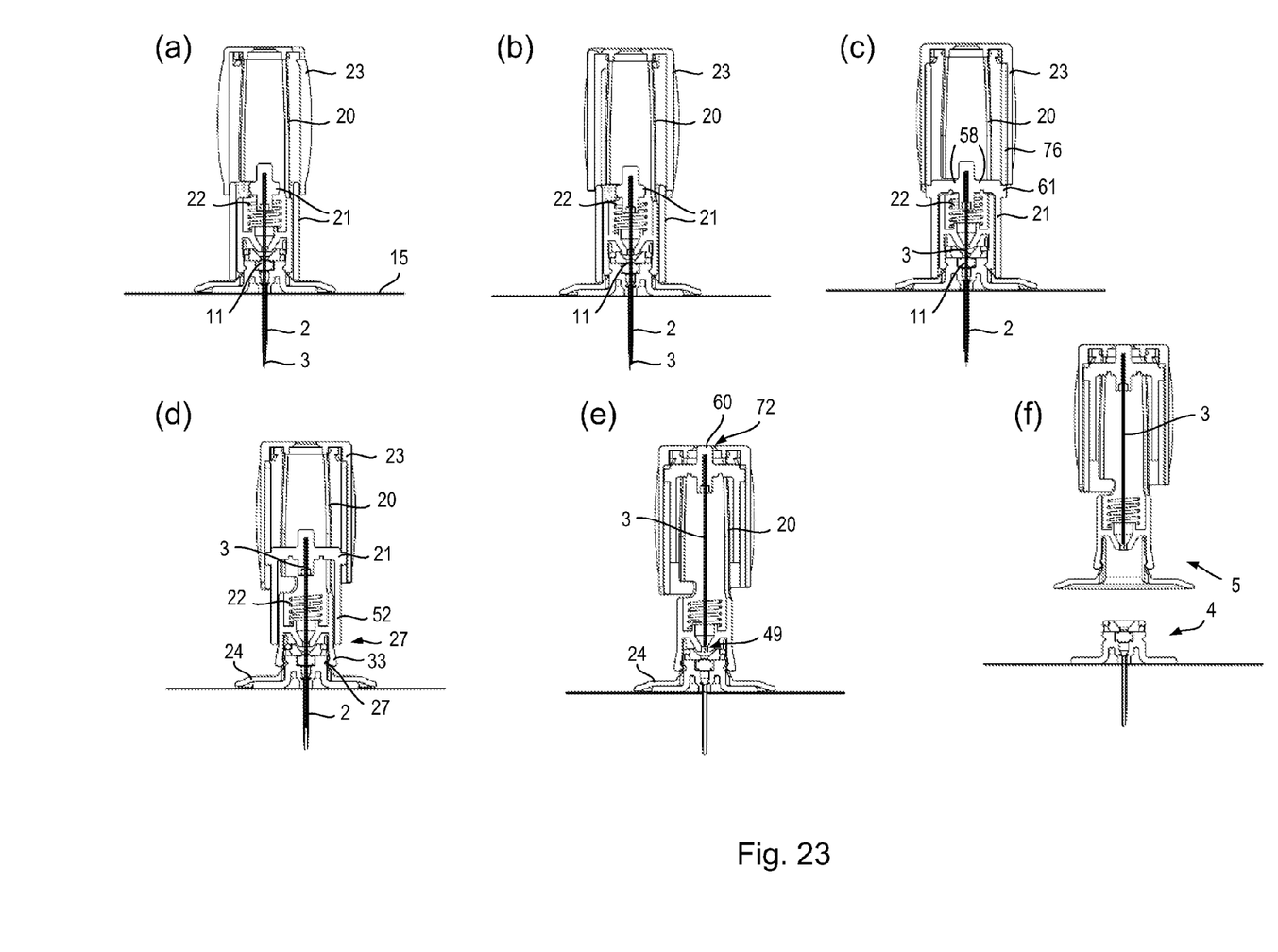

Referring in particular to FIGS. 22*a* and 23*a*, the user can place, for example their thumb and index finger or their index finger and middle finger of one hand, on the ribbed regions 50 of the chassis 20.

Using their other hand, the user takes the actuator cap 23 between their thumb and index finger and starts to twist the actuator cap 23, in this case, anticlockwise.

The actuator cap 23 is rotated. However, this rotation does not rotate the slider 21.

Referring to FIGS. 22*b* and 23*b*, after the actuator cap 23 has been rotated by 45°, the force-transmitting surfaces 71 (i.e. end of the cut-out 69) come into contact with the force-receiving members 61 (i.e. bosses).

The actuator cap 23 is rotated. Now rotation of the actuator cap 23 causes the slider 21 to rotate. As the slider 21 rotates, cross members 58 (FIG. 12) which are disposed at the start 37 (FIG. 11) of the slot 36 (FIG. 11) rotate and move along the first section 40 (FIG. 11) of the slot 36 (FIG. 11). Rotation of the slider 21 also causes the needle 3 to rotate which can help to avoid stiction.

Referring to FIGS. 22*c* and 23*c*, after the actuator cap 23 has been rotated by a further 45°, the cross members 58 (FIG. 12) reach the elbow 38 (FIG. 11) of the slot 36 (FIG. 11) and clear the corner 42 (FIG. 11). The force-receiving members 61 reach the bottom of the grooves 76. The spring 22 applies upward bias to the slider 21.

Referring to FIGS. 22*d* and 23*d*, the slider 21 is pushed upwards by the spring 22, away from the base 24 of the chassis 20. As the slider 21 moves, the needle 3 is retracted. Furthermore, as the slider 21 moves, the tubular body 52 begins to clear the lower section 27 of the chassis 20. Thus, the tubular body 52 no longer retains the barbed heads 33 of the catches 29 in the grooves 17.

Referring to FIGS. 22*e* and 23*e*, the slider 21 continues to be pushed upwards by the spring 22 and away from the base 24 of the chassis 20 until the distal end of the needle 3 is withdrawn beyond the aperture 49 inside the chassis 20.

In this position, the needle 3 is safely retracted, shielded by the chassis 20. This is confirmed to the user by the fact that indicator 60 appears in the window 72 at the top of the actuator cap 23. Successful retraction is also signalled to user by an audible click and also by haptic feedback in the form of a perceivable click.

Referring to FIGS. 22*f* and 23*f*, the hub assembly 4 and the needle retracting device 5 can be separated with the needle 3 is safely retracted.

Thus, in the course of a quarter turn (i.e. 90° turn) of the actuator cap 23, the user can conveniently retract the needle 3.

It will be appreciated that many modifications may be made to the embodiments hereinbefore described.

For example, the catheter assembly may be configured to operate in the opposite way, i.e. by rotating the actuator cap 23 (FIG. 23*a*) clockwise.

Different angles of rotation can be used, for example, such that the needle 3 (FIG. 5) is retracted in less than a quarter turn.

The second section 41 (FIG. 11) of the slot may be inclined, i.e. include not only a lengthwise component but also a circumferential component. Thus, the slider may continue to rotate as it is retracted.

The spring 22 may be omitted. For example, the chassis 20, slider 21, and actuator cap 23 may be configured to operate in a similar way to lipstick dispenser. Thus, twisting the cap 23 or an end actuator is used to draw back the slider 21 and withdraw the needle 3. A non-return latch (not shown) may be included to prevent the slider 21 from being pushed forward again.

Figure 18:
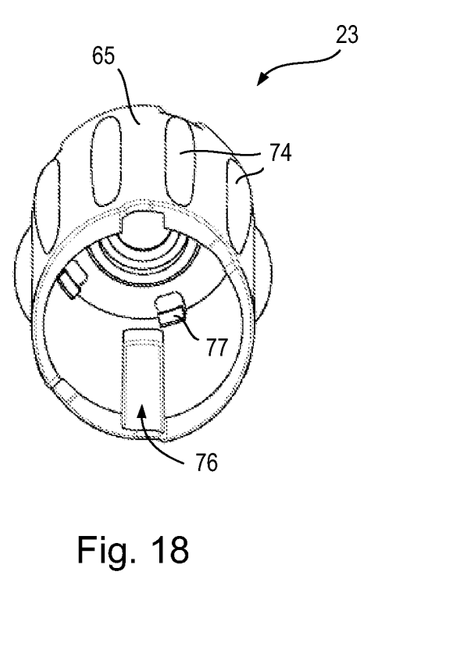
FIG. 18 is a bottom perspective view of the actuator cap shown in FIG. 16.
Figure 19:
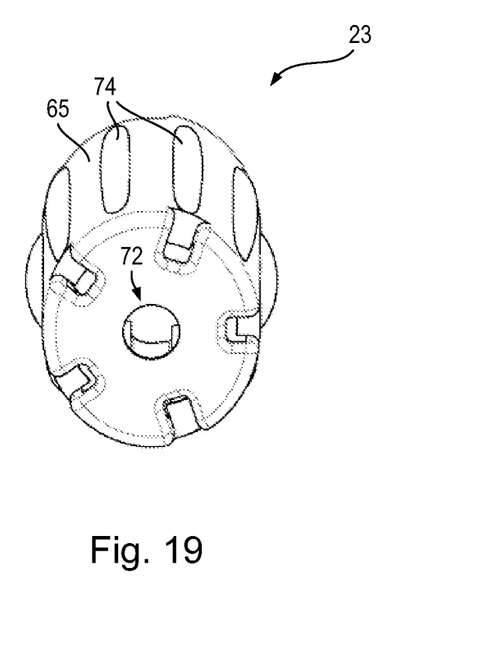
FIG. 19 is a top perspective view of the actuator cap shown in FIG. 16.

The slider 21 (FIG. 12) may include only one force-receiving member 61 (FIG. 12) or may include more than two (for example, three) force-receiving members 61 (FIG. 12). Accordingly, the actuator cap 23 (FIG. 17) may have a corresponding number of cut-outs 69 (FIG. 17), force-transmitting surfaces 71 (FIG. 17) and grooves 76 (FIG. 18).

The catches 29 (FIG. 18) may be inwardly biased and/or need not have a sloping outer surface. Thus, the inner wall 63 (FIG. 14) of the slider 21 (FIG. 14) need not urge the catches 29 (FIG. 18) inwards to engage the grooves 17 (FIG. 6). Thus, the inner wall 63 of the slider 21 may simply provide a barrier which discourages or prevents the catches 29 from disengaging from the grooves 17.

The surfaces for retaining (or urging and retaining) the catches 29 (FIG. 18) may take the form of depending fins. In other words, a continuous collar or skirt need not be used.

While the invention has been described in relation to placing a catheter for administering a drug subcutaneously, it will be appreciated that the assembly can be used or modified, for example by elongating the catheter, chassis and needle, for administering a drug intravenously, for example into the central line.

The invention claimed is:

1. A catheter assembly comprising:
   a hub assembly comprising a hub and a catheter attached to the hub; and
   a needle retracting device releasably attached to hub assembly which is arranged to project a needle through the catheter to allow catheterization and, in response to user actuation, to retract the needle and to be detached or to allow detachment from the hub assembly, the needle retracting device comprising:
      a chassis extending along an axis from a base; and
      a slider carrying the needle supported on the chassis, arranged to be moveable away from the base along the axis from a first position in which the needle projects through the catheter to a second position in which the needle is withdrawn from the catheter and is shielded by the chassis;
   wherein the chassis and hub comprise movable locking members and cooperating locking surfaces for engaging the locking members and wherein the slider comprises retaining surfaces for limiting movement of the locking members,
   wherein the catheter assembly is configured such that:
      when the slider is in the first position, the locking members are discouraged or prevented from disengaging from the locking surfaces by the retaining surfaces; and
      when the slider is in the second position, the locking members are free to disengage from the locking surfaces and so allow the needle retracting device to disengage from the hub assembly;
   wherein the chassis comprises:
      a tubular body extending from the base portion to a distal end along the axis; and the slider comprises:
      a tubular body disposed outside the tubular body of the chassis;
      a hub carrying the needle; and
      member(s) connecting the hub to the tubular body of the slider,
      wherein an inner wall of the tubular body of the slider provides the retaining surfaces.

2. A catheter assembly according to claim 1, wherein the chassis comprises the locking members and the hub comprises the locking surfaces.

3. A catheter assembly according to claim 1, wherein the locking members each comprise:
   a catch comprising a hinged arm and a barbed head.

4. A catheter assembly according to claim 1, wherein the locking surfaces each comprise:
   a recess.

5. A catheter assembly according to claim 1, wherein the tubular body of the chassis comprises:
   slots for receiving and guiding the member(s) connecting the hub to the tubular body of the slider;
   wherein each slot comprising a start, a first section and a second section, wherein the first section extends from the start and the second follows the first section, wherein the second section extends away from the base portion towards the distal end and is orientated so as to allow the slider to move along the tubular body.

6. A catheter assembly according to claim 5, wherein the first section is orientated so as to allow the slider to rotate within the tubular body of the chassis without moving along the tubular body.

7. A catheter assembly according to claim 1, further comprising:
   a cap-like actuator disposed over the distal end of the tubular body of the chassis and a distal end of the slider, wherein the actuator is configured to rotate starting from a first angular position and wherein rotational movement is communicable to the slider.

8. A catheter assembly according to claim 7, wherein the slider and actuator are configured such that rotational movement of the actuator from a first angular position to a second angular position is not communicated to the slider.

9. A catheter assembly according to claim 8, wherein the slider and actuator are configured such that rotational movement of the actuator from the second angular position to a third angular position is communicated to the slider and causes rotation of the slider without substantial movement along the tubular body of the chassis.

10. A catheter assembly according to claim 9, wherein the slider and actuator are configured such that further rotational movement from the third angular position causes the slider to move along the tubular body of the chassis.

11. A catheter assembly according to claim 7, wherein the actuator includes a window and the slider includes an indicator, the actuator and slider configured such that the indicator appears in the window when the slider is in the second position.

12. A catheter assembly according to claim 1, further comprising a spring biasing the slider away from the base.

13. A catheter assembly according to claim 1, wherein the hub assembly includes a port in fluid communication with the catheter.

* * * * *